US009606110B2

(12) United States Patent
Gittins et al.

(10) Patent No.: US 9,606,110 B2
(45) Date of Patent: Mar. 28, 2017

(54) DIAGNOSTIC ORAL DEVICE

(71) Applicant: Colgate-Palmolive Company, New York, NY (US)

(72) Inventors: Elizabeth Gittins, Stewartsville, NJ (US); Harsh M. Trivedi, Hillsborough, NJ (US); Sharon Kennedy, Randallstown, MD (US); Madhusudan Patel, Somerset, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/569,179

(22) Filed: Dec. 12, 2014

(65) Prior Publication Data

US 2015/0087074 A1    Mar. 26, 2015

Related U.S. Application Data

(62) Division of application No. 13/518,980, filed as application No. PCT/US2010/061704 on Dec. 22, 2010, now Pat. No. 8,920,340.

(60) Provisional application No. 61/289,425, filed on Dec. 23, 2009.

(51) Int. Cl.
A46B 11/00    (2006.01)
A46B 15/00    (2006.01)
A61B 10/00    (2006.01)
G01N 33/52    (2006.01)

(52) U.S. Cl.
CPC .......... *G01N 33/528* (2013.01); *A46B 11/001* (2013.01); *A46B 15/0002* (2013.01); *A46B 15/0048* (2013.01); *A46B 15/0055* (2013.01); *A61B 10/0051* (2013.01); *G01N 33/525* (2013.01); *A61B 2010/0006* (2013.01); *G01N 2800/18* (2013.01)

(58) Field of Classification Search
CPC .............. A46B 11/001; A46B 15/0002; A46B 15/0048; A46B 15/0055; A61B 10/0051; A61B 2010/0006; G01N 33/525; G01N 33/528; G01N 2800/18
See application file for complete search history.

(56) References Cited

U.S. PATENT DOCUMENTS

| 2,154,209 | A | 4/1939 | Kohn |
| 4,538,631 | A | 9/1985 | Prince |
| 4,753,249 | A | 6/1988 | Muller |
| 5,000,193 | A | 3/1991 | Heelis et al. |
| 5,458,563 | A | 10/1995 | Stewart |
| 5,463,792 | A | 11/1995 | Hogan et al. |
| 5,578,023 | A | 11/1996 | Schneider |
| 5,842,248 | A | 12/1998 | Van Grol et al. |
| 5,910,122 | A | 6/1999 | D'Angelo |
| 6,303,081 | B1 | 10/2001 | Mink et al. |
| 6,533,734 | B1 | 3/2003 | Corley, III et al. |
| 6,623,698 | B2 | 9/2003 | Kuo |
| 6,663,679 | B1 | 12/2003 | Duncan |
| 7,282,181 | B2 | 10/2007 | Hudak et al. |
| 7,449,001 | B2 | 11/2008 | Stoltz |
| 7,845,944 | B2 | 12/2010 | DiGasbarro |
| 8,202,230 | B2 | 6/2012 | Gatzemeyer et al. |
| 2003/0045814 | A1 | 3/2003 | Sangha |
| 2003/0053938 | A1 | 3/2003 | Szeles |
| 2003/0120180 | A1 | 6/2003 | Kaylor et al. |
| 2004/0071594 | A1 | 4/2004 | Malone et al. |
| 2004/0082878 | A1 | 4/2004 | Baldwin et al. |
| 2004/0097834 | A1 | 5/2004 | Stoltz |
| 2004/0220498 | A1 | 11/2004 | Li et al. |
| 2005/0221401 | A1 | 10/2005 | Nomura et al. |
| 2005/0244794 | A1 | 11/2005 | Kemp et al. |
| 2006/0141421 | A1 | 6/2006 | Braunecker et al. |
| 2006/0225744 | A1 | 10/2006 | Braunecker et al. |
| 2006/0280650 | A1 | 12/2006 | Wong et al. |
| 2007/0151575 | A1 | 7/2007 | De Masi, Sr. |
| 2007/0173738 | A1 | 7/2007 | Stoltz |
| 2007/0255177 | A1 | 11/2007 | Pronovost |
| 2008/0060148 | A1 | 3/2008 | Pinyayev et al. |
| 2008/0176183 | A1 | 7/2008 | Gatzemeyer et al. |
| 2009/0012425 | A1 | 1/2009 | Dodge et al. |
| 2009/0293211 | A1 | 12/2009 | Spungin |
| 2009/0306543 | A1 | 12/2009 | Slowey et al. |
| 2010/0331725 | A1 | 12/2010 | Libby et al. |

FOREIGN PATENT DOCUMENTS

| EP | 0097904 | | 1/1984 |
| JP | 2002-181812 | * | 6/2002 |
| JP | 2003-250631 A | | 9/2003 |
| JP | 2004-108858 A | | 4/2004 |
| JP | 2005-257604 A | | 9/2005 |
| JP | 2009-216497 A | | 9/2009 |
| KR | 2009-0090914 A | | 8/2009 |
| WO | WO 2004/084752 | | 10/2004 |
| WO | WO 2005/073721 | | 8/2005 |
| WO | WO 2008/139324 | | 11/2008 |
| WO | WO 2011/079166 | | 6/2011 |

OTHER PUBLICATIONS

Machine generated English translation of JP 2009-216497, downloaded on May 14, 2016.*
Etienne et al., 2006, "Polyelectrolyte Multilayer Film Coating and Stability at the Surfaces of Oral Prosthesis Base Polymers: An in vitro and in vivo Study," J. Dental Research 85(1):44-48.
Green et al., 1999, *Protective Groups in Organic Synthesis*, New York, NY pp. 67-74 and 708-711.
International Search Report and Written Opinion in International Application No. PCT/US10/061704, mailed Apr. 19, 2011.

(Continued)

*Primary Examiner* — Robert Landsman
*Assistant Examiner* — Bruce D Hissong

(57) ABSTRACT

Described herein are devices and methods for identifying the existence of an oral condition in a subject.

15 Claims, 1 Drawing Sheet

(56) References Cited

OTHER PUBLICATIONS

International Search Report and Written Opinion in International Application No. PCT/US10/061708, mailed Jul. 5, 2011.

International Search Report in International Application No. PCT/US09/054582, mailed Aug. 21, 2009.

Tangerman, 2002, "Halitosis in Medicine: A Review," International Dental J. 52(Supp. 3):201-206.

Written Opinion in International Application No. PCT/US10/061704, mailed Jan. 27, 2012.

\* cited by examiner

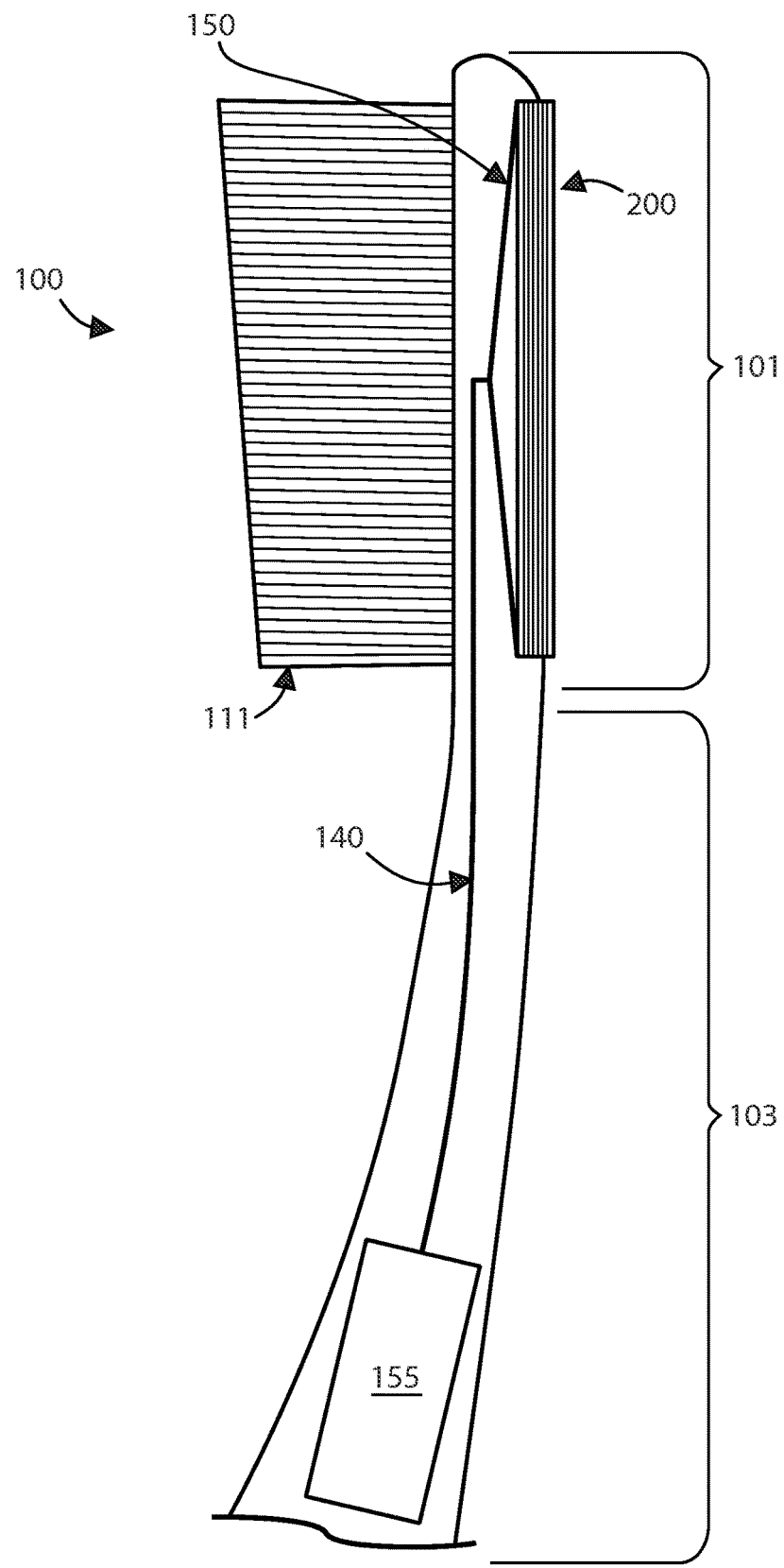

DIAGNOSTIC ORAL DEVICE

CROSS REFERENCE TO RELATED APPLICATIONS

This application is a divisional of U.S. patent application Ser. No. 13/518,980, filed Jun. 25, 2012, now allowed, which is a national stage entry under 35 U.S.C. §371 of International Patent Application No. PCT/US2010/061704, filed Dec. 22, 2010, which claims priority to U.S. Provisional Patent Application No. 61/289,425, filed on Dec. 23, 2009, all of which are incorporated in their entireties by reference herein.

BACKGROUND

Oral health problems can take many forms, such as tooth decay, periodontal disease, and bad breath. Bacteria plays a major role in many oral health issues. For example, tooth decay and periodontal disease are often caused by undesirable bacteria in the mouth. Bacteria also interact with proteins present in saliva to form a film, known as plaque, that coats the teeth. If this plaque is not removed, acids produced by the bacteria can attack the teeth resulting in tooth decay. The plaque also may attack the soft gum tissue of the mouth leading to tooth loss in adults.

Prior attempts at oral healthcare detection systems have been widely adopted and have had limited functionality. For example, test strips employing conventional approaches for diagnosing the risk of dental caries using antibodies to detect the presence of oral bacteria have not achieved commercial success or widespread adoption by the public. Moreover, systems using color as an indicator of the presence of particular bacteria or enzymes have been burdened by the need for additional processing or apparatus, e.g., a colorimeter or fluorometer, to develop the color. In addition to the inconvenience of performing multiple steps, the use of additional agents and equipment may increase risk and increases cost.

SUMMARY

Some embodiments of the present invention provide a device for identifying the existence of an oral condition, comprising: a vessel for collecting a sample from the oral cavity; a detector capable of detecting the existence of a marker within said sample; and an indicator capable of being actuated by a signal from the detector.

Further embodiments provide a method for identifying the existence of an oral condition in a subject comprising: collecting a sample from the oral cavity of a subject using a vessel; detecting the existence of one or more markers in the sample; and indicating the existence of at least one of the one or more markers to the subject.

BRIEF DESCRIPTION OF THE DRAWING

FIG. 1 is a schematic fragmentary cross-sectional illustration of a toothbrush construction according to an embodiment of the invention.

DETAILED DESCRIPTION

Some embodiments of the present invention provide a device for identifying the existence of an oral condition, comprising: a vessel for collecting a sample from the oral cavity; a detector capable of detecting the existence of a marker within the sample; and an indicator capable of being actuated by a signal from the detector. In other embodiments, the vessel is detachably secured to an oral care implement. In further embodiments, the vessel comprises a bioadhesive.

In some embodiments, the vessel comprises a collecting member and a reservoir. In some embodiments, the collecting member collects the sample from the oral cavity. In some embodiments, the reservoir stores the sample from the oral cavity. In some embodiments, the vessel contains a fluid pathway fluidly connecting the collecting member with the reservoir to provide the oral fluid to the reservoir. In some embodiments, the detector is disposed within the vessel. In certain embodiments, the indicator is disposed within the vessel.

In some embodiments, the detector is disposed within the reservoir. In some embodiments, the indicator is disposed within the reservoir.

FIG. 1 schematically illustrates a toothbrush 100 having a collecting member 200 and a reservoir 155 provided for storing an oral fluid medium, such as saliva and/or a mixture of saliva and dentifrice. In some embodiments, the reservoir 155 can be provided in the neck portion 105 of a toothbrush 100 or at the distal end of the toothbrush handle 103.

In some embodiments, a fluid pathway 140, such as a capillary channel, extends in the longitudinal direction of the toothbrush 100 for delivering the sample from the oral cavity to the reservoir 155 from at least one inlet 150. In some embodiments, the channel 140 uses capillary action to draw the sample from the inlet 150 to the reservoir 155. In some embodiments, the capillary channel 140 has a capillary structure. In certain embodiments, the channel 140 is in the form of a porous material. Examples of porous materials include fibrous materials, ceramics, and porous plastics such as those available from Porex Technologies, Atlanta, Ga. One example of a fibrous material is an acrylic material known as type number C10010, available from Teibow Hanbai Co., Ltd., Tokyo, Japan. In some embodiments, a mixture of porous and/or fibrous materials may be provided which have a distribution of larger and smaller capillaries. In some embodiments, the channel 140 can be formed from a number of small capillaries that are connected to one another, or as a larger single capillary tube.

In some embodiments, the sample in the reservoir 155 is analyzed for an oral disease, disorder or condition that is amenable to detection via examination of the oral cavity.

In some embodiments, the reservoir comprises a replaceable cartridge. In some embodiments, the vessel further comprises a receiver coupled to the collection member adapted to receive the sample from the oral cavity.

In some embodiments, the fluid pathway includes a fibrous material, ceramic, porous plastic, or combination thereof, for providing capillary recovery of a sample from the oral cavity.

In some embodiments, the sample is saliva, gingival crevicular fluid, or tissue. In some embodiments, the marker is indicative of poor oral care. In other embodiments, the marker is selected from the group consisting of: IL-1β, PGE2, arginine and gingipains.

In some embodiments, the indicator is a dye. In some embodiments, the indicator is exhausted after a single detection event. In some embodiments, the indicator is a structural indicator.

In some embodiments, the oral care implement is a tooth brush. In other embodiments, the oral care implement is dental floss.

In some embodiments, the vessel, detector and indicator are disposed within a patch. In other embodiments, the patch is capable of being secured to a surface of the oral cavity.

Some embodiments of the present invention provide a method for identifying the existence of an oral condition in a subject comprising: collecting a sample from the oral cavity of a subject using a vessel; detecting the existence of one or more markers in said sample; and indicating the existence of at least one of said one or more markers to said subject.

In some embodiments, the sample is saliva, gingival crevicular fluid, or tissue.

In some embodiments, the vessel comprises a filter. In some embodiments, the vessel is detachably secured to an oral care implement. In other embodiments, the vessel comprises a bioadhesive.

In yet other embodiments, at least one of said one or more markers is indicative of poor oral care. In further embodiments, at least one of said one or more markers is selected from the group consisting of: IL-1β, PGE2, arginine and gingipains.

In some embodiments, the indicator is a dye. In other embodiments, the indicator is exhausted after a single detection event. In some embodiments, the indicator is a structural indicator. In some embodiments, the indicator will demonstrate the existence of a particular marker immediately after exposure to the marker. In some embodiments, the indicator will demonstrate the existence of a particular marker about 2 days after exposure to the marker. In other embodiments, the indicator will demonstrate the existence of a particular marker after a threshold quantity of marker is detected.

In further embodiments, the oral care implement is a toothbrush. In certain embodiments, the oral care implement is dental floss. In some embodiments, the oral care implement is a dental pick. In some embodiments, the oral care implement is a tongue scraper.

In some embodiments, the vessel, detector and indicator are housed within a single structure. In some embodiments the structure within which the vessel, detector and indicator are housed is a zeolite or a patch. In some embodiments, the vessel, detector and indicator are disposed within a patch. In some embodiments, the patch is capable of being secured to a surface of the oral cavity.

In some embodiments, the device is a 'stand alone' device, to be used separately from an oral care implement. In some embodiments, the device may be embedded into a larger structure that fits over one or more teeth. In some embodiments, the device is incorporated into a brace, mouth-guard, dentures, or other device designed for placement within the mouth or over one or more teeth for an extended period of time.

In other embodiments, the indicator comprises a flavoring agent. In further embodiments, the indicator comprises a structural indicator. In some embodiments, the structural indicator provides an indication to the subject that a particular marker is present in the oral cavity. In some embodiments, the marker is specific to a particular disease, condition, or disorder. In some embodiments, the structural indicator is palpably perceptible by the subject. In some embodiments, the structural indicator is visually perceptible to the subject. In certain embodiments, the structural indicator is a pit. In other embodiments, the structural indicator is a ridge.

In some embodiments, the detector comprises one or more polymers. Suitable polymers are known in the art, including those described in Etienne O et al. (Polyelectrolyte multilayer film coating and stability at the surfaces of oral prosthesis base polymers: an in vitro and in vivo study. J Dent Res. 2006 Jan., 85(1): 44-8), which is incorporated herein by reference in its entirety.

In some embodiments, the indicator is insulated from oral cavity fluids and/or air. In some embodiments, the indicator may not be visible immediately after detection of a marker. In some embodiments, the indicator requires the continued presence of a marker to become visible.

In some embodiments, the oral conditions identified by the devices described herein include, but are not limited to, conditions associated with poor oral care, conditions which may be diagnosed by examination of the oral cavity, and systemic conditions which have been recognized or otherwise identified by the American Dental Association to be correlated with poor oral care.

In some embodiments, the condition is selected from the group consisting of: caries; gingivitis; periodontitis; halitosis; and dry mouth. In some embodiments, IL-1β, PGE2, arginine and gingipains are markers for gingivitis. In other embodiments, gingivitis is indicated by elevated levels of one or more of *P. gingivalis, C. gingivalis, P. melaninogenica, Treponema denticola, Bacterioides forsythus* and *S. mitis*. In some embodiments, halitosis is indicated by the presence of volatile sulfur compounds, including methyl mercaptan, dimethylsulfide and hydrogen sulfide, in the oral cavity.

In certain embodiments, periodontitis is indicated by the presence of elastases, dipeptidylpeptidase, β-glucuronidase, lactoferrin, platelet-activating factor (PAF), ICPT (pyridinoline cross-linked carboxyterminal telopeptide), cathepsin B (a cysteine protease), cystatins, MMP-1, collagenase-2 (matrix metalloproteinase, MMP-8), MMP-13 (collagenase-3), gelatinase (MMP-9), hydroxyl-deoxyguanosine and immunoglobulins such as IgA, IgG and IgM, in the oral cavity.

In other embodiments, the presence of bone-related biomarkers such as calprotectin, osteocalcin, ostenocetin and osteopontin, is associated with periodontal disease. In some embodiments, caries is indicated by low salival pH, local pH (i.e at specific locations on the hard tissue) and by acid-producing oral bacteria (specifically *Lactobacillus* species, *Streptococcus mutans*, and *Actinomyces* species).

In some embodiments, non-oral based systemic diseases are associated with oral malodor. In some embodiments, the non-oral based systemic diseases associated with oral malodor are: chronic liver failure; lower respiratory tract infections (bronchial and lung infections); renal infections and renal failure; and trimethylaminuria ("fish odor syndrome") (see reference: Tangerman A. Halitosis in medicine: a review. *Int Dent J.* 2002 June; 52 Suppl 3:201-6). In some embodiments, the marker may be detected in exhaled gases. In some embodiments, high concentrations of acetone (known as "acetone breath") in a subject's breath, indicates diabetic ketoacidosis.

In some embodiments, the systemic disease, disorder or condition may be a human pathological state, inflammation or cancer. In some embodiments, the marker is a bacterial metabolite marker, such as those described in PCT/US2009/039184; which is incorporated herein by reference in its entirety.

In some embodiments, the intensity of color demonstrated by the indicator correlates with the severity or prevalence of a disease or disorder. In some embodiments, the dye is selected from the group consisting of: tartrazine, amaranath, allura red, erythrosine B, indigo carmine, brilliant blue FCF, beta-carotene, fast green FCF, erioglaucine disodium salt, curcumin, chromotrope FB, new coccine, riboflavin 5'monophosphate sodium salt, riboflavin, betanin, lycopene, chocolate brown HT, brilliant black BN, green S, indogtine, bixin, brilliant scarlet 4R, amaranath, carmoisine azorubine, cochineal and sunset yellow FCF.

It will be understood that while the invention has been described in conjunction with specific embodiments thereof, the foregoing description is intended to illustrate, but not limit the scope of the invention. Other aspects, advantages and modifications will be apparent to those skilled in the art to which the invention pertains, and these aspects and modifications are within the scope of the inventions described and claimed herein.

What is claimed is:

1. A method for identifying the existence of an oral condition in a subject comprising:
    inserting an oral care implement having a vessel detachably secured thereto into an oral cavity of the subject;
    collecting a sample from the oral cavity of the subject using the vessel;
    detecting the existence of one or more markers in said sample; and
    indicating the existence of at least one of said one or more markers to said subject;
    wherein the oral care implement comprises a head and a handle, the head having a front surface with tooth cleaning elements extending therefrom and a rear surface, and wherein said vessel comprises:
        a collection member for collecting the sample from the oral cavity located on the rear surface of the head of the oral care implement;
        a reservoir for storing said sample located in the handle of the oral care implement; and
        a fluid pathway fluidly connecting the collection member with the reservoir to provide the sample to the reservoir.

2. The method of claim 1, wherein said vessel comprises a bioadhesive.

3. The method of claim 2 further comprising a detector for detecting the existence of one or more markers in said sample and an indicator for indicating the existence of at least one of said one or more markers, wherein said vessel, detector and indicator are disposed within a patch.

4. The method of claim 3, wherein said patch is capable of being secured to a surface of the oral cavity.

5. The method of claim 1, further comprising a detector disposed within said reservoir for detecting the existence of the one or more markers in said sample.

6. The method of claim 1, further comprising an indicator disposed within said reservoir for indicating the existence of at least one of said one or more markers.

7. The method of claim 1, wherein said sample is saliva, gingival crevicular fluid, or tissue.

8. The method of claim 1, wherein at least one of said one or more markers is indicative of poor oral care.

9. The method of claim 8, wherein at least one of said one or more markers is selected from the group consisting of: interleukin-1 beta ("IL-1β"), prostaglandin E2 ("PGE2"), arginine and gingipains.

10. The method of claim 1, further comprising an indicator for indicating the existence of at least one of said one or more markers, wherein said indicator is a dye.

11. The method of claim 1, further comprising an indicator for indicating the existence of at least one of said one or more markers, wherein said indicator is exhausted after a single detection event.

12. The method of claim 1, further comprising an indicator for indicating the existence of at least one of said one or more markers, wherein said indicator is a structural indicator.

13. The method of claim 1, wherein said oral care implement is a tooth brush.

14. A method for identifying the existence of an oral condition in a subject comprising:
    inserting an oral care implement having a vessel detachably secured thereto into an oral cavity of the subject;
    collecting a sample from the oral cavity of the subject using the vessel;
    detecting the existence of one or more markers in said sample; and
    indicating the existence of at least one of said one or more markers to said subject;
    wherein said oral care implement is dental floss.

15. A method for identifying the existence of an oral condition in a subject comprising:
    inserting an oral care implement having a vessel detachably secured thereto into an oral cavity of the subject;
    collecting a sample from the oral cavity of the subject using the vessel;
    detecting the existence of one or more markers in said sample; and
    indicating the existence of at least one of said one or more markers to said subject;
    wherein the vessel comprises:
        a collection member for collecting the sample from the oral cavity;
        a reservoir for storing said sample, an indicator disposed within the reservoir;
        a fluid pathway formed of a capillary material fluidly connecting the collection member with the reservoir to provide the sample to the reservoir by capillary action.

* * * * *